United States Patent

Moyer et al.

[11] 4,078,118
[45] Mar. 7, 1978

[54] PENTAERYTHRITOL ESTERS OF MERCAPTO ACIDS PLUS LONG CHAIN FATTY ACIDS

[75] Inventors: Joseph Donald Moyer, Silver Spring; David Edward Kramm, Laurel, both of Md.

[73] Assignee: W. R. Grace & Co., New York, N.Y.

[21] Appl. No.: 780,566

[22] Filed: Mar. 23, 1977

Related U.S. Application Data

[62] Division of Ser. No. 623,216, Oct. 16, 1975, Pat. No. 4,039,723.

[51] Int. Cl.$^2$ ............... C08L 81/02; C08L 91/00; C08F 2/46; C08F 2/50
[52] U.S. Cl. .................. 428/521; 204/159.15; 204/159.23; 260/23.5 R; 260/79.5 C; 260/399; 260/410
[58] Field of Search ............ 204/159.23, 159.15; 260/23.5 R, 79.5 C, 399; 428/521

[56] References Cited

U.S. PATENT DOCUMENTS

| | | | |
|---|---|---|---|
| 3,547,961 | 12/1970 | Onozuka et al. | 260/399 |
| 3,661,744 | 9/1972 | Kehr et al. | 204/159.23 X |
| 3,833,519 | 9/1974 | Ejk et al. | 260/23 X A |
| 3,898,349 | 8/1975 | Kehr et al. | 427/36 |

FOREIGN PATENT DOCUMENTS

7,309,449  1/1974  Netherlands.

*Primary Examiner*—Walter C. Danison
*Attorney, Agent, or Firm*—Richard P. Plunkett; William W. McDowell, Jr.

[57] ABSTRACT

This invention relates to compositions of the formula:

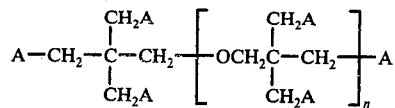

wherein n is 0 to 2 and at least 1 and not more than 2n + 2 of the A groups are ester radicals of the structure

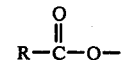

wherein R is a straight chain or branched, saturated or unsaturated hydrocarbon radical containing 11 to 19 carbon atoms and at least 2 and not more than 2n + 3 of the A groups are ester radicals of the structure

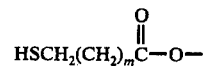

wherein m is 0 to 1.

The composition is formed by reacting one mole of a mono-, di- or tri-pentaerythritol of the formula:

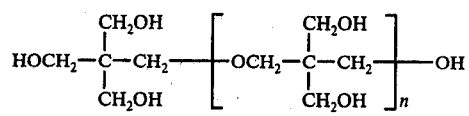

wherein n is 0-2 with 2n + 4 moles of a mixture of monocarboxylic acids from the group consisting of (a) at least 1 and not more than 2n + 2 moles of RCOOH wherein R is a straight chain or branched, saturated or unsaturated hydrocarbon radical containing 11 to 19 carbon atoms and (b) at least 2 and not more than 2n + 3 of HSCH$_2$(CH$_2$)$_m$COOH wherein m is 0 to 1. In the present invention it is preferred to react only one acid from each of the mercapto and the long chain fatty acid group members. However, more than one acid from each group member can be reacted if desired.

6 Claims, No Drawings

PENTAERYTHRITOL ESTERS OF MERCAPTO ACIDS PLUS LONG CHAIN FATTY ACIDS

This is a division of application Ser. No. 623,216 filed Oct. 16, 1975, now U.S. Pat. No. 4,039,723.

This invention relates to pentaerythritol esters. More particularly, this invention relates to pentaerythritol esters used in radiation curable coatings which impart improved slip characteristics contributed by the fatty acid moiety present in the instant pentaerythritol esters.

The use of radiation curable compositions in roll coating substrates has gained wide interest. This is due to the fact that in many cases no solvent is necessary and, therefore, solvent recovery and its adjunct pollution problems are not present. Further, radiation curable coatings do away with the necessity of heating or drying ovens and their concurrent problems of pollution and high energy requirements.

The object of the instant invention is to provide a pentaerythritol ester which when used in combination with a polyene can provide a radiation curable coating which has improved slip, i. e., lubricity, characteristics.

The above and other objects are obtained herein by a pentaerythritol ester composition of the formula:

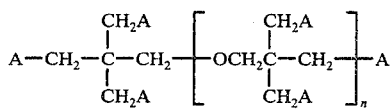

wherein $n$ is 0 to 2 and at least 1 and not more than $2n + 2$ of the A groups are ester radicals of the structure

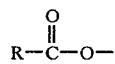

wherein R is a straight chain or branched, saturated or unsaturated hydrocarbon radical containing 11 to 19 carbon atoms and at least 2 and not more than $2n + 3$ of the A groups are ester radicals of the structure

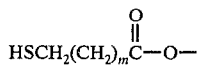

wherein $m$ is 0 to 1.

The composition is formed by reacting one mole of a mono, di- or tri-pentaerythritol of the formula:

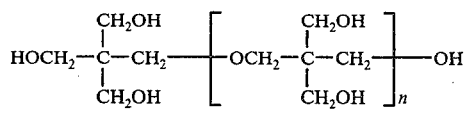

wherein $n$ is 0-2 with $2n + 4$ moles of a mixture of monocarboxylic acids from the group consisting of (a) at least 1 and not more than $2n + 3$ moles of RCOOH wherein R is a straight chain or branched, saturated or unsaturated hydrocarbon radical containing 11 to 19 carbon atoms and (b) at least 2 and not more than $2n + 3$ of $HSCH_2(CH_2)_mCOOH$ wherein $m$ is 0 to 1. In the present invention it is preferred to react only one acid from each of the mercapto and the long chain fatty acid group members. However, more than one acid from each group member can be reacted if desired.

Operable fatty acids of the formula RCOOH herein include, but are not limited to, lauric, myristic, palmitic, stearic, isostearic, oleic, linoleic and arachidic acid·β-mercaptopropionic and mercaptoacetic acid are the operable mercapto acids in this invention.

The reaction is preferably carried out in a solution which forms an azeotrope with water. Aliphatic or aromatic hydrocarbon solvents such as hexane, benzene, xylene and the like are operable as solvents in the instant invention.

In practicing the invention, an acid catalyst, e. g., p-toluene sulfonic acid, methane sulfonic acid, sulfuric acid and the like, is employed in catalytic amounts.

The reaction is performed at the refluxing temperature of the mixture. The reaction period is from about 16 to 48 hours depending upon reactants and catalysts employed.

In carrying out the reaction the solvent, pentaerythritol, catalyst and the mercapto and the long chain fatty acids are added concurrently to the reactor. The reactor is then heated to the reflux temperature of the mixture with stirring and the reaction is continued until water is no longer evolved indicating completion of the reaction. Although the mercapto and the long chain fatty acid can be added concurrently in practicing the invention, the acids can also be added sequentially. That is, for example, one could add the fatty acid to the reactor containing the pentaerythritol, solvent and catalyst, heat the reactor to the refluxing temperature of the mixture with stirring and continue the reaction until water is no longer evolved. At this point one could then add the mercapto acid, maintain the reaction at the refluxing temperature of the mixture with stirring and continue the reaction until water was no longer evolved. On completion of the reaction the mixture becomes a homogeneous solution.

The amount of acid added can range from the stoichiometric amount within the range set forth supra up to an amount in excess thereof, e. g., 20% excess.

Following the reaction, the ester product is recovered by washing with water or washing with an aqueous base followed by a water wash and thereafter removing the solvent by stripping under vacuum or other conventional means.

The following examples will explain, but expressly not limit, the instant invention. Unless otherwise noted, all parts and percentages are by weight.

EXAMPLE 1

Dipentaerythritol (1.20 mols, 305 gms), stearic acid (1.32 mols, 375 gms), 2000 ml of toluene, and 12 gms of p-toluenesulfonic acid were combined in a 5-liter 3-neck flask equipped with stirrer, Dean Stark trap and addition funnel. The mixture was stirred and heated to vigorous refluxing until no longer collected in the trap. This required 4 hours reaction time, and a total of 21 ml of water was collected. Using the additional funnel, 700 grams (6.60 mols) of β-mercaptopropionic acid was added all at one time. Heating and refluxing was continued until water was no longer evolved, requiring 16 hours additional reaction time. The reaction mixture became a homogeneous solution at this time. After cooling the mixture was washed successively with 2500 ml distilled water, 2500 ml of 5% NaHCO₃ solution, and 2 × 2500 ml of water. The toluene solution containing the product was separated and dried with anhydrous MgSO$_4$, treated with about 5 gms of decolorizing carbon and filtered through a Celite-coated filter. The toluene was flashed off on a rotary evaporator, with water aspiration, then finally stripped with a high vacuum pump through a liquid N$_2$ cooled trap. The viscous yellowish residue gradually changed to a waxy semisolid on cooling. The resultant product weighed 1125 g. (96% yield) and analyzed 4.68 meq. of SH/g. The theoretical SH for the structure of the product:

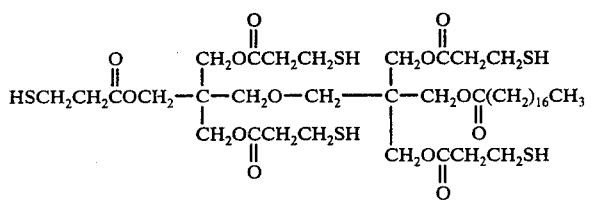

is 5.20 meq. SH/g.

EXAMPLE 2

To a glass-lined steam jacketed reactor piped up in series with a heat exchanger, decanter and pump to allow recycling of the solvent and water withdrawal was charged 350 pounds benzene, 100.3 pounds triple pressed stearic acid, 118.2 pounds β-mercapto proprionic acid, 50 pounds pentaerythritol and 5.4 pounds of p-toluene sulfonic acid. The reactants were mixed for one hour at which time heat was applied to raise the temperature to 185°-190° F. The reaction was continued under refluxing conditions with stirring for 37 hours at which time the acid number was 0.174. The reactor was cooled to room temperature and the contents of the reactor was subjected to repeated batch washes with deionized water until the acid number was 0.031. The solvent was then stripped from the reaction at a temperature of about 165–170° F under vacuum over a period of four hours. The resulting product weighed 238 pounds (87% yield) and analyzed for 4.44 meq. SH/g. and 0.077 meq. acid/g. The theoretical SH for the structure of the product:

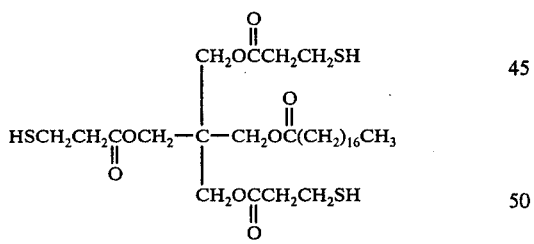

is 4.50 meq. SH/g.

EXAMPLE 3

A glass-lined steam jacketed reactor equipped with stirrer was piped up in series with a heat exchanger, decanter and pump which allowed the solvent to be recycled back to the reactor. To the reactor was charged 600 pounds toluene, 130 pounds of dipentaerythritol (containing 22.13 meq. OH/g.), 132 pounds of triple pressed stearic acid (containing 3.63 meq. carboxyl/g.), 7.8 pounds of p-toluene sulfonic acid and 259 pounds of β-mercapto propionic acid (containing 9.25 meq. OH/g.). The decanter was filled with 72.5 pounds of toluene to aid recycle. Stirring was commenced and the reactor was heated in the range 210°-216° F for a period of 22 hours. The reactor was cooled down and repeated washes of deionized water were charged to the reactor until the acid number of the reaction was 0.01. The reactor was then reheated to 165° F and the toluene solvent was stripped off under vacuum. The resultant product was collected and weighed 425 pounds (76.6% yield) and analyzed for 4.82 meq. SH/g. and 0.013 meq. acid/g. The theoretical SH for the structure of the product:

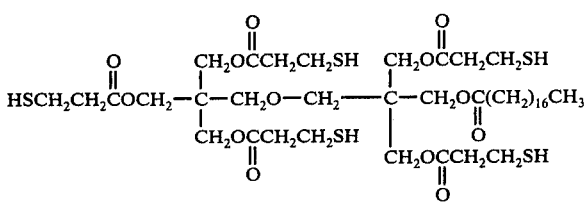

is 5.20 meq. SH/g.

The fatty acid-containing pentaerythritol esters of the instant invention can be used in conjunction with polyenes to form radiation curable coatings having improved slip properties. The polyenes operable herein include, but are not limited to, those disclosed in U.S. Pat. No. 3,661,744 and U.S. Pat. No. 3,898,349, both incorporated herein by reference.

Generally stated, the present invention provides a curable composition of improved slip properties which comprises 98 to 2 percent by weight of said composition of a polyene component and 2 to 98 percent by weight of said composition of a polythiol, i. e., fatty acid-containing pentaerythritol ester, component. A photosensitizer is added when curing is by U. V. light.

The polyene component may be represented by the formula:

$$[A \!\!+\!\! X]_m$$

wherein $m$ is an interger of at least 2, wherein X is a member selected from the group consisting of:

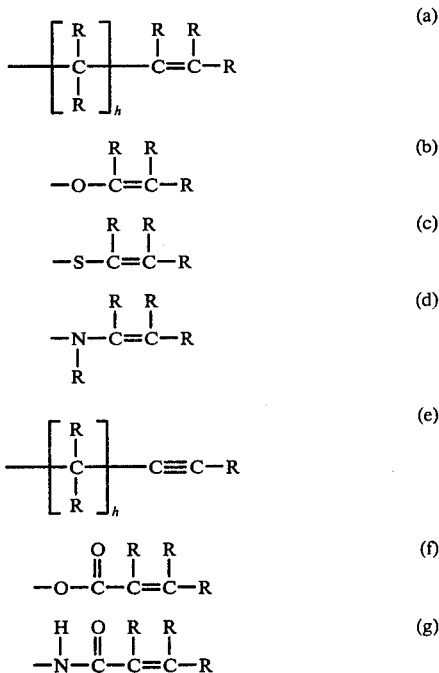

In the groups (a) to (g), $h$ is an integer from 1 to 9; R is a radical selected from the group consisting of hydrogen, fluorine, chlorine, furyl, thienyl, pyridyl, phenyl, and substituted phenyl, benzyl and substituted benzyl, alkyl and substituted alkyl, alkoxy and substituted alkoxy, and cycloalkyl and substituted cycloalkyl. The substituents on the substituted members are selected from the group consisting of nitro, chloro, fluoro, acetoxy, acetamide, phenyl, benzyl, alkyl, alkoxy and cycloalkyl. Alkyl and alkoxy have from one to nine carbon atoms and cycloalkyl has from three to eight carbon atoms.

The members (a) to (g) are connected to [A] through divalent chemically compatible derivative members. The members (a) to (g) may be connected to [A] through a divalent chemically compatible derivative member of the group consisting of $Si(R)_2$, carbonate, carboxylate, sulfone,

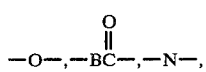

alkyl and substituted alkyl, cycloalkyl and substituted cycloalkyl, urethane and substituted urethane, urea and substituted urea, amide and substituted amide, amine and substituted amine, and aryl and substituted aryl. The alkyl members have from one to nine carbon atoms, the aryl members are either phenyl or naphthyl, and the cycloalkyl members have from three to eight carbon atoms with R and said members substituted being defined above. B is a member of the group consisting —O—, —S—, and —NR—.

The member [A] is a polyvalent; free of reactive carbon-to-carbon unsaturation, free of highly water-sensitive members; and consisting of atoms selected from the group consisting of carbon, oxygen, nitrogen, chlorine, bromine, fluorine, phosphorus, silicon and hydrogen. Said atoms are combined to form chemically compatible members of the group consisting of carbonate, carboxylate, carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, hydroxyl, heterocyclic carbon containing radical, and mixtures thereof; said substituents on said members being defined above.

The polyene component has a molecular weight in the range from about 64 to 20,000, preferably about 200 to about 10,000; and a viscosity in the range from essentially 0 to 20 million centipoises at 70° C as measured by a Brookfield Viscometer.

The member [A] of the polyene composition may be formed primarily of alkyl radicals, phenyl and urethane derivatives, oxygenated radicals, and nitrogen substituted radicals. The member [A] may also be represented by the formula:

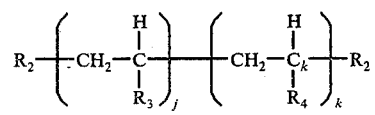

wherein $j$ and $k$ are integers greater than 1; $R_2$ is a member of the group consisting of hydrogen and alkyl having one to nine carbon atoms; $R_3$ is a member of the group consisting of hydrogen and saturated alkyl having one to nine carbon atoms; $R_4$ is a divalent derivative of the group consisting of phenyl, benzyl, alkyl, cycloalkyl, substituted phenyl, substituted benzyl, substituted alkyl and substituted cycloalkyl; with the terms alkyl, cycloalkyl and members substituted being defined above.

Representative formulas for polyenes operable in the present invention may be prepared as exemplified below:

I. Poly (alkylene-ether) Polyol Reacted with Unsaturated Monoisocyanates Forming Polyurethane Polyenes and Related Polymers Trifunctional

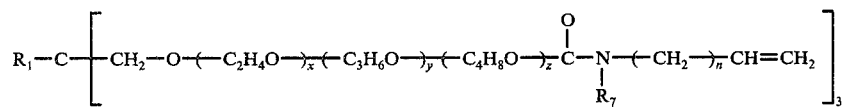

Tetrafunctional

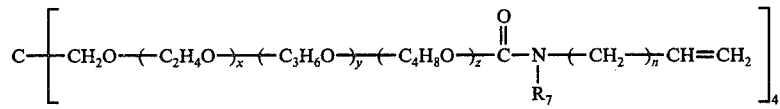

Tri-to-Hexafunctional

-continued

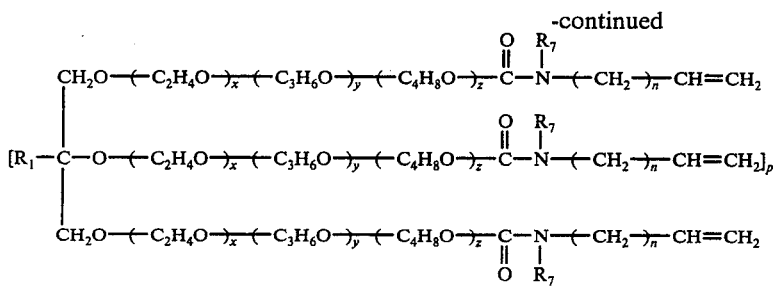

Interconnected-Modified Tetrafunctional

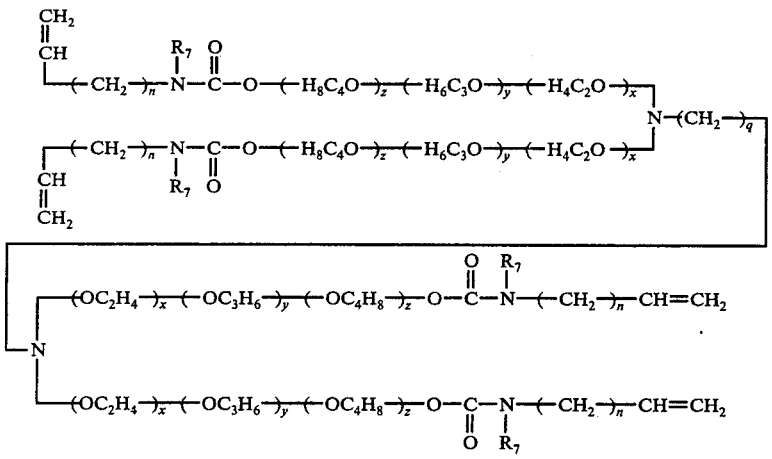

II. Poly (alkylene-ether)Polyol Reacted with Polyisocyanate and Unsaturated Monoalcohol Forming Polyurethane Polyenes and Related Polymers Trifunctional

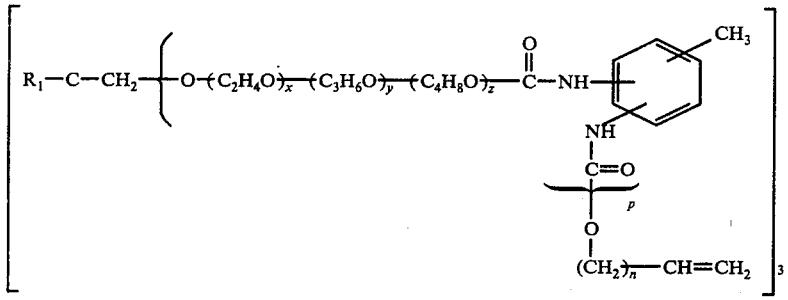

In the above formulas, the sum of $x + y + z$ in each chain segment is at least 1; $p$ is an integer of 1 or more; $q$ is at least 2; $n$ is at least 1; $R_1$ is selected from the group consisting of hydrogen, phenyl, benzyl, alkyl, cycloalkyl, and substituted phenyl; and $R_7$ is a member of the group consisting of $CH_2\!=\!CH\text{-}(CH_2)_n$, hydrogen, phenyl, cycloalkyl, and alkyl.

The class of polyenes of this invention derived from carbon-to-carbon unsaturated monoisocyanates may be characterized by extreme ease and versatility of manufacture when the liquid functionality desired is greater than about three. For example, consider an attempted synthesis of a polyhexene starting with an -OH terminated polyalkylene ether hexol such as "Niax" Hexol LS-490 (Union Carbide Corp.) having a molecular weight of approximately 700, and a viscosity of 18,720 cps at 20° C. An attempt to terminate this polymer with ene groups by reacting 1 mole of hexol with 6 moles of tolylene diisocyanate (mixed-2,4, 2-6-isomer product) and 6 moles of allyl alcohol proceeded nicely but resulted in a prematurely chain extended and crosslinked solid product rather than an intended liquid polyhexene. Using the monoisocyanate route, however, this premature chain extension may be avoided and the desired polyurethane-containing liquid polyhexene may be very easily prepared by a simple, one-step reaction of one mole of hexol with 6 moles of allyl isocyanate. This latter polyhexene has the added advantage of being cured using the teachings of this invention to a non-yellowing polythioether polyurethane product. Similarly, the unsaturated monoisocyanate technique may be used to prepare liquid polyenes from other analagous highly functional polyols such as cellulose, polyvinyl alcohol, partially hydrolized polyvinyl acetate, and the like, and highly functional polyamines such as tetraethylene pentamine, polyethyleneimine, and the like.

A general method of forming one type of polyene containing urethane groups is to react a polyol of the general formula $R_{11}$(OH)$_n$ wherein $R_{11}$ is a polyvalent organic moiety free from reactive carbon-to-carbon unsaturation and $n$ is at least 2 with a polyisocyanate of the general formula $R_{12}$(NCO)$_n$ wherein $R_{12}$ is a polyvalent organic moiety free from reactive carbon-to-carbon unsaturation and $n$ is at least 2 and a member of the group consisting of an ene-ol, yne-ol, ene-amine and yne amine. The reaction is carried out in an inert moisture-fre atmosphere (nitrogen blanket) at atmospheric pressure at a temperature in the range from 0° to about 120° C for a period of about 5 minutes to about 25 hours. In the case where an ene-ol or yne-ol is employed, the reaction is preferably a one step reaction. Where an ene-amine or yen-amine is used, the reaction is preferably a two step reaction wherein the polyol and the polyisocyanate are reacted together and thereafter preferably at room temperature, the ene-amine or yne-amine is added to the NCO terminated polymer formed. The group consisting of ene-ol, yne-ol, ene-amine and yne-amine are usually added to the reaction in an amount such that there is one carbon-to-carbon unsaturation in the group member per hydroxyl group in the polyol and said polyol and group member are added in combination in a stoichiometric amount necessary to react with the isocyanate groups in the polyisocyanate.

A second general method of forming a polyene containing urethane groups (or urea groups) is to react a polyol (or polyamine) with an ene-isocyanate or an yne-isocyanate to form the corresponding polyene. The general procedure and stoichiometry of this synthesis route is similar to that described for polyisocyanates in the preceding. In this instance, a polyol reacts with an ene-isocynanate to form the corresponding polyene. It is found, however, that products derived from this route, when cured in the presence of an active light source and a polythiol, may form relatively weak solid polythioether products. To obtain stronger cured products, it is desirable to provide polar functional groupings within the main chain backbone of the polymeric polyene. These polar functional groupings serve as connecting linkages between multiple repeating units in the main chain series, and serve as internal strength-reinforcing agents by virtue of their ability to create strong interchain attraction forces between molecules of polymer in the final cured composition.

Another group of polyenes operable in this invention includes those polyenes in which the reactive unsaturated carbon-to-carbon bonds are conjugated with adjacent unsaturated groupings. Examples of operable reactive conjugated ene systems include, but are not limited to the following:

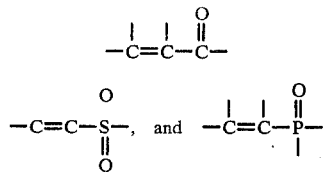

A few typical examples of polyenes which contain conjugated reactive double bonds groupings such as those described above are the triacrylate of the reaction product of trimethylolpropane with 20 moles of ethylene oxide, pentaerythritol tetraacrylte, trimethylolpropane trimethacrylate and triacrylate, triacrylate of isocyanurate, tetramethaacrylate, and the like.

The aforesaid polyenes containing ester groups may be formed by reacting an acid of the formula $R_{13}$(COOH)$_n$ wherein $R_{13}$ is a polyvalent organic moiety free from reactive carbon-to-carbon unsaturation and $n$ is at least 2, with either an ene-ol or yne-ol. The reaction is carried out at atmospheric pressure at a temperature in the range from 0° to about 120° C for a period of 5 minutes to 25 hours. Usually the reaction is carried out in the presence of a solvent, e.g., benzene at refluxing temperature. The water formed is azeotroped off of the reaction.

Another method of making an ester containing polyene is to react a polyol of the formula $R_{11}$(OH)$_n$ wherein $R_{11}$ is a polyvalent organic moiety free from reactive carbon-to-carbon unsaturation and $n$ is at least 2; with either an ene-acid or an yne-acid. The reaction is carried out in the same manner as set out above for the ester-containing polyenes.

A further group of polyenes which are operable in the present invention includes unsaturated polymers in which the double or triple bonds occur also within the main chain of molecules. These are derived primarily from standard diene monomers such as polyisoprene, butadiene, styrene-butadiene rubber, isobutylene-isoprene rubber, polychloroprene, styrene-butadiene-acrylonitrile rubber and the like unsaturated polyesters, polyamides, and polyurethanes derived from monomers containing "reactive" unsaturation. As examples, adipic acid-butenediol, 1,6-hexanediamine-fumaric acid and 2,4-tolylene diisocyanatebutenediol condensation polymers and the like are operable.

In forming the polyenes of the present invention, catalytic amounts of a catalyst may be employed to speed up the reaction. This is especially true in the case where an ene-ol is used to form the polyene. Such catalysts are well known to those in the art and include organometallic compounds such as stannous octoate, stannous oleate, dibutyl tin dilaurate, cobalt acetylacetonate, ferric acetylacetonate, lead naphthanate and dibutyl tin diacetate. The polyene/polythiol mole ratios are selected so as to provide a solid, self-supporting cured product under ambient conditions in the presence of actinic or high energy ionizing radiation.

The curing reaction can be initiated by either U. V. radiation or high energy ionizing radiation. The U. V. radiation can be obtained from sunlight or special light sources which emit significant amounts of U. V. light having a wavelength in the range of about 2000 to 4000 Angstrom units. When U.V. radiation is used for the curing reaction, a dose of 0.0004 to 60 watts/centimeter$^2$ is employed.

When U.V. radiation is used for curing, a photosensitizer is added to the composition. Preferred photocuring rate accelerators or photosensitizers are the aldehyde and ketone carbonyl compounds having at least one aromatic nucleus attached directly to the

group. Various photosensitizers include, but are not limited to, benzophenone, acetophenone, o-methoxybenzophenone, acenapthenequinone, methyl ethyl ketone, valerophenone, hexanophenone, γ-phenylbutyrophenone, p-morpholinopropiophenone, dibenzosuberone, 4-morpholinobenzophenone, 4'morpholinodeoxybenzoin, p-diacetylbenzene, 4-aminobenzophenone, 4'-methoxyacetophenone, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,5-triacetylbenzene, thioxanthen-9-one, xanthene-9-one, 7-H-benz[de]anthracen-7-one, 1-naphthaldehyde, 4,4'-bis(dimethylamino) benzophenone, fluorene-9-one, 1'-acetonaphthone, 2'-acetonaphthone, 2,3-butanedione, triphenylphosphine, tri-o-tolyphosphine, acetonaphthone, 2,3-butanedione, benz[a]anthracene 7,12 dione, etc. which serve to give greatly reduced exposure times and thereby when used in conjunction with various forms of energetic radiation yield very rapid, commercially practical time cycles by the practice of the instant invention. The photosensitizers are usually added in an amount ranging from 0.0005 to 50% by weight of the polyene and polythiol.

The radiation curable compositions of the instant invention can also be cured by high energy ionizing irradiation. A preferred feature of the ionizing irradiation operation of the instant invention is treatment with high energy particle irradiation or by gamma-rays or X-rays. Irradiation employing particles in the instant invention includes the use of positive ions, (e.g., protons, alpha particles and deuterons), electrons or neutrons. The charged particles may be accelerated to high speeds by means of various voltage gradient mechanisms such as a Van de Graaff generator, a cyclotron, a Cockroft Walton accelerator, a resonant cavity accelerator, a betatron, a G.E. resonant transformer, a synchrotron or the like. Furthermore, particle irradiation may also be supplied from radioactive isotopes or an atomic pile. Gamma rays or X-rays may be obtained from radioisotopes (e.g. cobalt 60) or by particle bombardment of suitable target material (e.g., high energy electrons on a gold metal target).

The dose rate for the irradiation operable to cure the coating in the instant invention is in the range 0.00001 to 1000 megarads/second.

The amount of ionizng radiation which is employed in curing the radiation curable material in the instant invention can vary between broad limits. Radiation dosages of less than a megarad up to 10 megarads or more for electrons are operable, preferably 0.02 to 5 megarads energy absorbed are employed. For gamma-rays or X-rays, radiation dosages in the range 0.0001 to 5.0 megarads energy absorbed are operable. The irradiation step is ordinarily performed under ambient temperature conditions but can be performed at temperatures ranging from below room temperatures up to temperatures of 90° C.

The compositions to be radiation cured, i.e., converted to solid coatings, in accord with the present invention may, if desired, include such additives as antioxidants, inhibitors, activators, fillers, pigments, dyes, antistatic agents, flame-retardant agents, thickeners, thixotropic agents, surface-active agents, viscosity modifiers, plasticizers, and the like within the scope of this invention. Such additives generally are preblended with the polyene of polythiol prior to coating it on the substrate. The aforesaid additives may be present in quantities up to 500 parts or more per 100 radiation curable compositions by weight and preferably 0.0005 to 300 parts on the same basis. The type and concentration of the additives must be selected with care so that the final composition remains radiation curable under conditions of exposure.

The curable liquid polymer compositions of the instant invention prior to curing can be pumped, poured, brushed, sprayed, doctored, rolled, trowelled, dipped-coated, extruded or gunned into place into cavities, into molds, or onto vertical or horizontal flat surfaces in a uniform fashion. Following such application curing in place to a solid resin or an elastomer can be made to occur very rapidly. The compositions can be applied to various substrates and adhere well to glass, wood, metals, concrete, certain plastics, paints, enamels, fabrics, paper, paper board, porcelain, ceramics, brick, cinder block, plaster and vinyl floor tile.

The liuid polythioether-forming components and compositions of the instant invention can, prior to curing, be admixed with or blended with other monomeric and polymeric materials such as thermoplastic resins, elastomers or thermosetting resin monomeric or polymeric compositions. The resulting blend can be subjected to conditions for curing or co-curing of the various components of the blend to give cured products having unusual physical properties. Examples of the classes of the materials which can be admixed, blended or co-cured with the polythioether-forming compositions of the instant invention are illustrated by, but not limited to, the following: epoxy resins, phenolic resins, polysulfide resins, and elastomers, polyurethane resins and elastomers, polyamide resins, polyvinylchloride resins, amphorous or crystalline polyolefins, polyacrylonitrile polymers, silicone polymers, urea-formaldehyde resins, polyether resins and elastomers and the like.

The solid cured polythioether polymer products resulting from the instant invention have many and varied uses. Examples of some uses include but are not limited to adhesives; caulks; elastomeric sealants, coatings, such as wire coatings, electrical circuits cover resists, photoresists and the like, encapsulating or potting compounds, liquid castable elastomers; thermoset resins, impregnants for fabric, cloth, fibrous webs and other porous substrates; laminating adhesives and coatings; mastics; glazing compounds; fiberglass reinforced composites; sizing or surface finishing agents, filleting compounds; cured in place gasketing compounds; rocket fuel binders; foamable thermosetting resins or elastomers; molded articles such as gaskets, diaphragms, ballons, automobile tires, etc.

The molecular weight of the polyenes of the present invention may be measured by various conventional methods including solution viscosity, osmotic pressure and gel permeation chromatography. Additionally, the molecular weight may ve calculated from the known molecular weight of the reactants.

The viscosity of the polyenes and polythiols may be measured on a Brookfiled Viscometer at 30° or 70° C in accord with the instructions therefor.

The components to be cured may be prepared as either single-packaged or multi-packaged liquid polymer systems which may be cured to solid polythioether elastomers without liberating gaseous by-products which cause bubbles and voids in the vulcanizate. Thus, there is provided curable liquid polymer systems composed of polyenes and polythiols in which the components individually are storage stable and which are not sensitive to or deteriorated by traces of moisture or oxygen containing gas such as may be encountered during normal storage or handling procedures. Solid resinous or elastomeric products may be prepared from flowable liquid in a system in which the rate of curing may be inhibited or retarded by the use of chemical inhibitors, antioxidants, and the like. Conventional curing inhibitors or retarders which may be used in order to stabilize the components or curable compositions so as to prevent premature onset of curing may include certain acids and bases; hydroquinone; p-tert-butyl catechol; 2,6-di-tert-butyl-p-methylphenol; phenothiazine; N-phenyl-2-naphthylamine; pyrogallol; octadecyl-β-(4-hydroxy-3,5-di-t-butyl phenyl)-propionate; and the like. The cured product may be characterized as in the thermally and oxidatively stable state since there is no reactive carbon-to-carbon unsaturation in the main backbone chain.

As used herein the term polyene and the term polyne refers to single or complex species of alkenes or alkynes having a multiplicity of terminal reaction carbon-to-carbon unsaturated functional groups per average molecule. For example, a diene is a polyene that has two reactive carbon-to-carbon double bonds per average molecule. Combinations of reactive double bonds and reactive triple bonds within the same molecule are also possible such as for monovinylacetylene which is a polyeneyne under this definition. For purposes of brevity all these classes of compounds are referred to herein as polyenes.

In defining the position of the reactive functional carbon-to-carbon unsaturation, the term terminal is intended to mean that functional unsaturation is at an end of the main chain in the molecule; whereas by near terminal is intended to mean that the functional unsaturation is not more than 10 carbon atoms and typically less than eight carbon atoms from an end of the main chain in the molecule. The term pendant means that the reactive carbon-to-carbon unsaturation is located terminal or near-terminal in a branch of the main chain as contrasted to a position at or near the ends of the main chain. For purposes of brevity all of these positions are referred to herein generally as terminal unsaturation.

Functionality as used herein refers to the average number of ene or thiol groups per molecule in the polyene or polythiol, respectively. For example, a triene is a polyene with an average of three reactive carbon-to-carbon unsaturated groups per molecule and thus has a functionality (f) of three. A dithiol is a polythiol with an average of two thiol groups per molecule and thus has a functionality (f) of two.

The mole ratio of ene/thiol groups for preparing the curable composition is from about 1/0.25 to about 1/4.0 and desirably about 1/0.75 to about 1/1.25 group ratio.

The following example will show the improved slip property obtained by the fatty acid containing pentaerythritol esters of the instant invention as compared with conventional commercially available pentaerythritol esters which do not contain the fatty acid moiety. The static and kinetic coefficient of friction was measured in accord with the procedure set out in ASTMD-1894-63.

EXAMPLE 4

The following formulations were made up and admixed until homogeneous.

| Formulation A | Parts |
|---|---|
| Component | by Weight |
| Diallyl phthalate | 48.8 |
| Pentaerythritol tetrakis β-(mercaptopropionate) | 48.8 |
| Fatty acid containing pentaerythritol ester product of Example 3 | 10.0 |
| Benzophenone (photocuring rate accelerator) | 2.0 |
| Antioxidant and thermal stabilizers | 0.4 |
| Formulation B | Parts |
| Component | by Weight |
| Diallyl phthalate | 35.5 |
| Fatty acid containing pentaerythritol ester product of Example 3 | 62.4 |
| Benzophenone | 2.0 |
| Antioxidant and thermal stabilizers | 0.4 |
| Formulation C | Parts |
| Component | by Weight |
| Diallyl phthalate | 48.8 |
| Pentaerythritol tetrakis β-(mercaptopropionate) | 48.8 |
| Benzophenone | 2.0 |
| Antioxidant and thermal stabilizers | 0.4 |

Each of the above formulations was coated onto two aluminum sheets in an amount equal to 8 mg./4 inches square. The thus coated sheets were then passed through a U.V. housing at the rate of 50 feet per minute wherein they are exposed to U.V. radiation at a surface irradiance of 110 milliwatts/cm$^2$ from 3 mercury vapor lamps. The aluminum sheets were then subjected to a second pass under the lamps at the same speed and irradiance. One sheet of each formulation was then subjected to baking in an air oven for 10 minutes at 375° F. The coefficient of friction results are shown in Table I.

Table I

|  | Coefficient of Friction | |
|---|---|---|
|  | Static | Kinetic |
| Formulation A | 0.224 | 0.196 |
| Formulation A (baked) | 0.196 | 0.187 |
| Formulation B | 0.260 | 0.230 |
| Formulation B (baked) | 0.310 | 0.250 |
| Formulation C | 0.383 | 0.374 |
| Formulation C (baked) | 0.392 | 0.350 |

As can be seen from the results, even the addition of a minor amount of the fatty acid-containing pentaerythritol esters (Formulation B) gives a marked improvement in slip as shown by the lower coefficient of friction as compared to the control (Formulation C) using a conventional pentaerythritol ester without any fatty acid moiety.

We claim:

1. A curable composition useful for obtaining a solid polythioether having improved slip properties comprising:

A. a polyene component of the formula:

$$[A\!\!+\!\!X]_m$$

wherein $m$ is an integer of at least 2, wherein X is a member selected from the group consisting of:

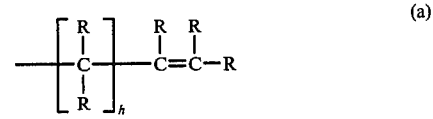

(a)

(b)

(c)

(d)

-continued

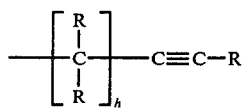(e)

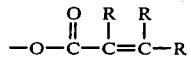(f)

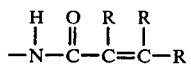(g)

where h is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonate, carboxylate, carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, hydroxyl, heterocyclic carbon containing radical, and mixtures thereof; said substituents on said members being defined above, said component having a molecular weight in the range from about 64 to 20,000; and a viscosity in the range from essentially 0 to 20 million centipoises at 70° C; and, B. pentaerythritol ester component of the formula:

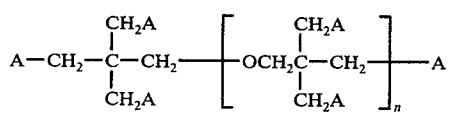

wherein n is 0 to 2, and at least 1 and not more than 2n + 2 of the A groups are ester radicals of the structure

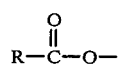

wherein R is a straight chain or branched, saturated or unsaturated hydrocarbon radical containing 11 to 19 carbon atoms, and at least 2 and not more than 2n + 3 of the A groups are ester radicals of the structure

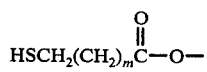

wherein m is 0 to 1 and
C. a photosensitizer.

2. A process for forming a solid, cured polythioether having improved slip properties which comprises admixing A. a polyene component of the formula:

wherein m is an integer of at least 2, wherein X is a member selected from the group consisting of:

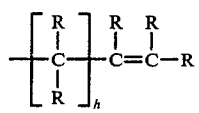(a)

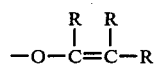(b)

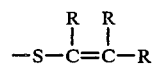(c)

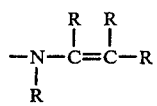(d)

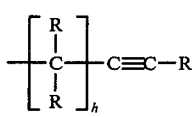(e)

(f)

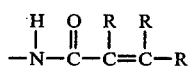(g)

where h is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cyloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonate, carboxylate, carbonyl, ether, silane, silicate, phosphate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, hydroxyl, heterocyclic carbon containing radical, and mixtures thereof; said substituents on said members being defined above, said component having a molecular weight in the range from about 64 to 20,000; and a viscosity in the range from essentially 0 to 20 million centipoises at 70° C;

B. pentaerythritol ester component of the formula:

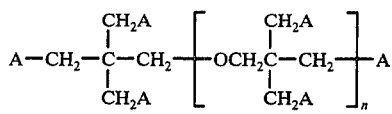

wherein n is 0 to 2, and at least 1 and not more than 2n + 2 of the A groups are ester radicals of the structure

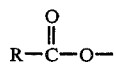

wherein R is a straight chain or branched, saturated or unsaturated hydrocarbon radical containing 11 to 19 carbon atoms, and at least 2 and not more than 2n + 3 of the A groups are ester radicals of the structure

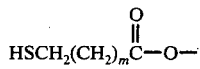

wherein m is 0 to 1; and

C. a photosensitizer, and thereafter exposing the mixture to actinic light.

3. The process according to claim 2 wherein the pentaerithritol ester is

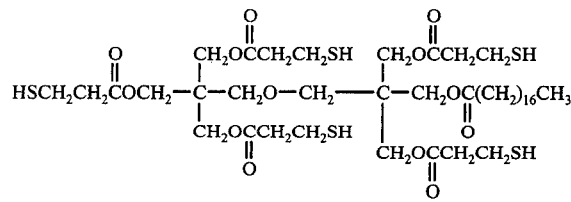

4. A process for forming a solid, cured polythioether having improved slip properties which comprises admixing A. a polyene component of the formula:

wherein m is an integer of at least 2, wherein X is a member selected from the group consisting of:

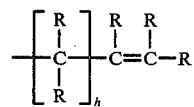 (a)

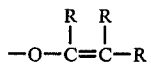 (b)

 (c)

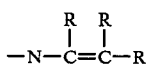 (d)

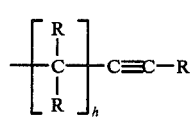 (e)

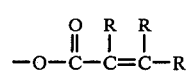 (f)

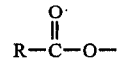 (g)

where h is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonate, carboxylate, carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, hydroxyl, heterocyclic carbon containing radical, and mixtures thereof; said substituents on said members being defined above, said component having a molecular weight in the range from about 64 to 20,000; and a viscosity in the range from essentially 0 to 20 million centipoises at 70° C; and B. pentaerythritol ester component of the formula:

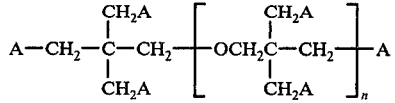

wherein n is 0 to 2, and at least 1 and not more than 2n + 2 of the A groups are ester radicals of the structure

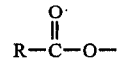

wherein R is a straight chain or branched, saturated or unsaturated hydrocarbon radical containing 11 to 19 carbon atoms, and at least 2 and not more than 2n + 3 of the A groups are ester radicals of the structure

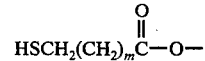

wherein m is 0 to 1, and thereafter exposing the mixture to high energy ionizing radiation.

5. The process according to claim 4 wherein the penthaerythritol ester is

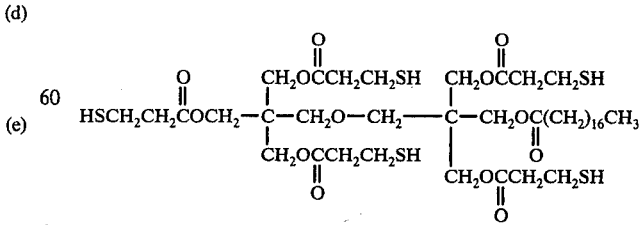

6. The composition of claim 1 as a coating on a substrate.

* * * * *

UNITED STATES PATENT OFFICE
CERTIFICATE OF CORRECTION

Patent No. 4,078,118　　　　　　　　Dated March 7, 1978

Inventor(s) J. Donald Moyer and David E. Kramm

It is certified that error appears in the above-identified patent and that said Letters Patent are hereby corrected as shown below:

In column 16, line 56, after the word "silicate" delete the word "phosphate" and insert therefor the word --phosphonate--.

Signed and Sealed this

Twenty-first Day of November 1978

[SEAL]

Attest:

RUTH C. MASON  
*Attesting Officer*

DONALD W. BANNER  
*Commissioner of Patents and Trademarks*